United States Patent [19]

Morris, Jr.

[11] 3,954,862

[45] May 4, 1976

[54] PROCESS FOR PRODUCING α-6-DEOXYTETRACYCLINES

[75] Inventor: Thomas A. Morris, Jr., Groton, Conn.

[73] Assignee: Pfizer Inc., New York, N.Y.

[22] Filed: Dec. 3, 1973

[21] Appl. No.: 421,206

Related U.S. Application Data

[63] Continuation-in-part of Ser. No. 353,084, April 20, 1973, abandoned.

[52] U.S. Cl. .......................................... 260/559 AT
[51] Int. Cl.² ......................................... C07C 103/19
[58] Field of Search .............................. 260/559 AT

[56] References Cited
UNITED STATES PATENTS 3,200,149   8/1965   Blackwood et al. ........... 260/559 AT

FOREIGN PATENTS OR APPLICATIONS 2,308,227   8/1973   Germany ..................... 260/559 AT

*Primary Examiner*—Joseph A. Narcavage
*Attorney, Agent, or Firm*—Francis X. Murphy; Charles J. Knuth; Albert E. Frost

[57] ABSTRACT

The catalytic hydrogenation of 6-methylenetetracyclines, or salts of these compounds, in a reaction-inert solvent medium containing a catalytic amount of rhodium metal to which a phosphine and a promoter is added.

25 Claims, No Drawings

PROCESS FOR PRODUCING α-6-DEOXYTETRACYCLINES

CROSS-REFERENCE TO RELATED APPLICATION

This application is a continuation in part of copending application Ser. No. 353,084, filed Apr. 20, 1973, and now abandoned.

FIELD OF THE INVENTION

The present process relates to a new and improved process for producing 6-deoxytetracyclines. More particularly, it comprises an improvement in the process of introducing hydrogen into a reaction-inert solvent medium containing a catalytic amount of rhodium metal and a 6-demethyl-6-deoxy-6-methylenetetracycline, the improvement comprising the addition of a phosphine and a promoter to the medium. The process achieves greater conversion of the 6-demethyl-6-deoxy-6-methylenetetracyclines to 6-deoxytetracyclines, enhanced ratios of α-6-deoxytetracyclines to β-6-deoxytetracyclines, and minimized formation of degradation products.

DESCRIPTION OF THE ART

U.S. Pat. No. 3,200,149 discloses and claims, inter alia, a novel group of tetracycline compounds which are generally designated as α-6-deoxytetracyclines. The process of U.S. Pat. No. 3,200,149 for producing α-6-deoxytetracyclines involves noble-metal (including rhodium) hydrogenation of a 6-demethyl-6-deoxy-6-methylenetetracycline to produce a mixture containing the corresponding α-6-deoxytetracycline and the corresponding β-6-deoxytetracycline. This reaction mixture is then separated to obtain the desired α-isomer. Under preferred operating conditions, the process is generally capable of producing up to about 1:1 mixture of α- to β-isomer. In view of the fact that the α-isomers, particularly α-6-deoxy-5-oxytetracycline, are of a higher order of activity than the corresponding β-isomers a significant improvement in the ratio of α- to β-isomer produced without substantial reduction in the yield of the mixture of isomers is of substantial importance.

An improved process for noble metal catalytic hydrogenation of 6-demethyl-6-deoxy-6-methylenetetracyclines which brings about an improvement in the α- to β-isomer ratio and enhanced yield of the mixture of isomers is described in U.S. Pat. No. 3,444,198. The process comprises conducting the reaction in the presence of a noble metal catalyst poisoned with carbon monoxide, quinoline-sulfur or any one of a variety of thiourea derivatives. The susceptibility of metal catalysts to poisons is pointed out by Maxted (Advan. Catalysis 3, 129, 1951). A variety of compounds of elements of Groups V-A and VI-A of the Periodic Classification of the Elements, including nitrogen, phosphorous, oxygen and sulfur compounds, are discussed as poisons.

The hydrogenation of unsaturated hydrocarbons acetylenes and olefins) in inert homogeneous liquid media by contacting the unsaturated hydrocarbon with hydrogen in the presence of a zerovalent compound of palladium or platinum which contains one or more tertiary phosphine ligands dissolved in the liquid media is described in U.S. Pat. No. 3,463,830. The zerovalent palladium or platinum compounds are prepared by reduction of divalent palladium or platinum compounds with hydrazine, usually in the presence of an excess of the tertiary phosphine.

German Application OS 2,308,227 describes the preparation of α-6-deoxytetracyclines by homogeneous catalytic hydrogenation using tris(triphenylphosphine)chlororhodium as catalyst. The catalyst can be performed or formed in the reaction mixture (in situ) by dissolving rhodium chloride and triphenylphosphine or other ligand in a suitable solvent together with the appropriate 6-demethyl-6-deoxy-6-methylenetetracycline substrate prior to introduction of hydrogen. In the case of in situ preparation of catalyst, molar proportions of triphenylphosphine, or other ligand, to rhodium (present initially as rhodium chloride) of less than 1:1 are reported to lead to formation of deposits of metal in powdered form which act as a heterogeneous catalyst with predominant formation of β-epimers rather than of the desired α-epimers. Molar ratios of triphenylphosphine, or other ligand, to metal of greater than 3:1 are reported to lead to homogeneous catalysts with incomplete conversion of substrate and, of course, reduced yields of the desired product.

Homogeneous catalytic hydrogenation of exocyclic methylene groups using tris(triphenylphospine)chlororhodium as catalyst in methylenecyclohexanes (Augustine et al., Ann. N.Y. Acad. Sci. 158, 482–91, 1969), coronopilin (Ruesch et al., Tetrahedron 25, 807–11, 1969); and in an intermediate in the stereoselective total synthesis of seychellene (Piers et al. Chem.Communs. 1069–70, 1969) is reported.

SUMMARY OF THE INVENTION

It has now been found that the process which comprises introducing hydrogen into a reaction-inert solvent medium containing a catalytic amount of rhodium metal and a 6-demethyl-6-deoxy-6-methylenetetracycline selected from the group consisting of

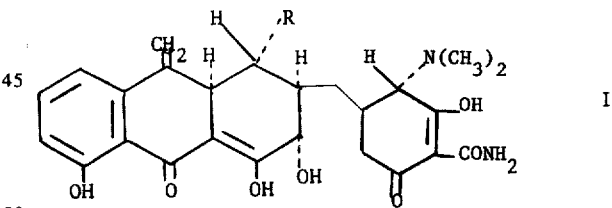

acid addition salts thereof and polyvalent metal salts thereof wherein R is selected from the group consisting of hydrogen and hydroxy at an appropriate temperature and pressure until reduction of the 6-methylene group occurs; is markedly improved by including a phosphine and a promoter in the reaction-inert solvent medium containing the catalyst and 6-methylenetetracycline reactant.

DETAILED DESCRIPTION OF THE INVENTION

In accordance with the process of this invention, hydrogen is introduced into a reaction-inert solvent medium containing a compound of formula I, or a salt thereof, a catalytic amount of rhodium metal, a promoter and a phosphine.

Thereafter, the α- to β- mixture produced is recovered by conventional procedures involving catalyst removal and recovery of the mixture from the solvent medium. This mixture is then subjected to chromatograhic or other known procedures; e.g., addition of sulfosalicylic acid to precipitate primarily the α-isomer as is described in J. Am. Chem. Soc. 84, 2643–51 (1963). A typical method of separation is included in the examples hereinafter.

The expression "reaction-inert solvent medium" refers to any medium which is a solvent or suitable suspending agent for the 6-methylene tetracycline reactant, is stable under the hydrogenation conditions, and does not interfere with the effectiveness of the catalyst or interact with the antibiotic. Polar organic solvents are generally suitable and include those enumerated in U.S. Pat. Nos. 3,200,149 and 3,444,198. As is the case in the process of those patents, basic media are undesirable since they tend to promote decomposition, reducing the yield of the desired product.

Excellent results are achieved in a wide range of reaction media including methanol, ethanol, acetone, methyl ethyl ketone, dioxane, formamide, monoalkyl - and dialkylformamides of one to four carbon atoms in each alkyl group (such as N-methylacetamide; N,N-dimethylacetamide; N-methyl, N-acetylformamide; N,N-diethylacetoacetamide), pyrrolidone, N-methyl-2-pyrrolidone, methyl 1-methyl-2-pyrrolidone-4-carboxylate, ethylene glycol, propylene glycol, 2-methoxyethanol, 2-ethoxyethanol, acetonitrile, acetic acid, tetramethylurea, tetrahydrofuran and gamma butyrolactone.

Mixtures of these solvents may also be employed. Preferred solvents for the reaction include methylformamide, N-methylacetamide, methyl 1-methyl-2-pyrrolidone-4-carboxylate and tetramethyl urea; and particularly preferred are methanol and N-methyl-2-pyrrolidone. Such solvents often give best results when they contain from about 5 to 80 volume percent water.

Particular virtues of the foregoing solvents include the following:

1. Rhodium metal, even prior to addition of the phosphine, remains relatively stable in these media. However, it is advisable to introduce the phosphine promptly when a solvent such as methanol is employed to avoid the possibility of catalyst degradation.

2. It is well known in the catalyst art that different lots of the same catalyst exhibit variable performance in their intended function. The enumerated media, however, have been found to give consistently high product yields even with so-called inferior catalyst batches.

3. Enhanced solubility provided by many of these media often permit the use of particularly high substrate concentrations, up to 30% by weight and more.

4. These media provide optimum results at relatively low weight ratios of catalyst to substrate, often at ratios of about 1:2 and lower.

5. Particularly high conversion of substrate, high yields of αisomer and predominant formation of α-isomer are afforded with these media.

6. Ease of recovery of high quality α-isomer.

As in other hydrogenations of tetracycline-type antibiotics, temperature is not a particularly critical condition so long as it is high enough to promote adequate reaction rates and does not become so high as to promote undesired by-product formation. In general, temperatures of from about 0° to about 100°C. are operable. At the lower end of this range, e.g. below about 10°C. the reaction is too slow to be of practical value. At the upper end of this range, e.g. at about 95°C. or higher, decomposition of reactanct and products occurs. Temperatures of from about 25°C. to about 90°C. are favored. Within this range, a temperature of from about 70° to 90°C. is particularly preferred.

The rhodium metal employed as catalyst in the present invention can be of the supported or non-supported type. Examples of suitable catalyst supports include carbon, silica, alumina and barium sulfate. The rhodium is preferably used in supported form, e.g., rhodium-on-carbon, rhodium-on-barium sulfate, rhodium-on-barium carbonate and rhodium-on-alumina. The particularly preferred form is 5% rhodium-on-carbon. The expression "Catalytic amount" as used herein is well understood by those skilled in the art of hydrogenations on tetracycline-type compounds and typical amounts are illustrated by the examples appearing hereinafter. Best results are usually achieved with from about 0.0001 to 2 parts by weight of catalyst (metal), dry basis, per part of substrate, although higher or lower ratios are also employed successfully. Typically, a 1:3 molar ratio of catalyst to 6-methylenetetracycline compound may be used. Rhodium-on-carbon, the preferred catalyst, is commercially available as a 50% wet (with water) mixture containing 5% rhodium-on-carbon (dry basis) and is conveniently used in this form.

The pressure employed during hydrogenation may range from subatmospheric to 2,000 p.s.i. or even higher if suitable equipment is available. Sub-atmospheric pressures down to 100 mm. Hg or even lower can be employed successfully, but for speed and convenience hydrogen pressures of one atmosphere or higher are usually preferred. In general, pressures ranging up to about 1,000 p.s.i. are quite adequate since they promote hydrogenation within a reasonable time.

The 6-methylenetetracycline compounds to be reduced may be in amphoteric form, in the form of polyvalent metal salt complexes (e.g. calcium, barium, zinc, magnesium), or pharmaceutically-acceptable or pharmaceutically-unacceptable acid addition salts of the compounds. Among the pharmaceutically-acceptable salts are those of mineral acids, including hydrochloric, hydriodic, hydrobromic, phosphoric, metaphosphoric, nitric and sulfuric acids. Also included are salts of organic acids such as tartaric, acetic, citric, malic, benzoic, glycollic, gluconic, succinic, arylsulfonic, e.g., p-toluenesulfonic, sulfosalicyclic acids and the like. The pharmaceutically-unacceptable acid addition salts include those of hydrofluoric acid and perchloric acid.

The 6-methylenetetracycline compounds (formula I) are preferably used as acid addition salts. The favored salts are the hydrochlorides, sulfosalicylates, p-toluenesulfonates, perchlorates and perborates.

The salts can be performed or can be formed in situ by addition of an equimolar amount of the appropriate acid to the reaction mixture containing the 6-methylenetetracycline base to form an acid addition salt. It has been observed that the rate of the hydrogenation reaction and the yield of the desired α-epimer are unexpectedly improved by the presence of an excess of acid over and above that required to form an acid addition salt with the 6-methylenetetracycline reactant. In other words, a molar ratio of acid to 6-methylenetetracycline base greater than 1:1 appears to exert a promoting effect upon reaction rate and yield. The excess acid; i.e., the amount of acid present beyond that required to form the acid addition salt of the 6-methylenetetracycline base, can be the same or different from that used to form the acid addition salt of the 6-methylenetetracycline. The important feature is that the total acid present be such as to provide a total molar ratio of acid to 6-methylenetetracycline base of from about 1.1 to 2.0. Alternatively, an excess of from about 0.1 to about 1.0 mole of acid per mole of 6-methylenetetracycline acid addition salt is favored. Total molar ratios of acid to 6-methylenetetracycline base of from about 1.5 to about 2.0 are preferred. The presence of a greater molar ratio, for example, even up to five moles of acid per mole of 6-methylenetetracycline base does not appear detrimental to the process. Para-toluene sulfonic acid and hydrochloric acid are especially useful as promoters.

Other substances also have a promoter effect on the reaction. In addition to the above-mentioned acids, it has been observed that stannous chloride exerts a pronounced promoter effect, even beyond that observed with the above-mentioned excesses of acids. Under a given set of conditions, the use of stannous chloride appears to be more effective than does p-toluenesulfonic acid in promoting the reaction. The use of other metal chlorides, such as those of platinum, cadmium, silver, lead, copper, sodium and mercury, are useful promoters for reactions wherein chloride is present. Lewis acids appear to function as promoters of the reaction.

Such promoters are generally used at levels of from about 0.1 mole to about 5 moles, per mole of 6-methylenetetracycline acid addition salt used. Higher levels appear to be of no value. The preferred range is from about 0.1 to about 1.0 mole per mole of 6-methylenetetracycline acid addition salt.

The phosphines of value in this improved process are those of the formula

wherein each of $R_1$ and $R_2$ is selected from the group consisting of phenyl and substituted phenyl wherein the substituent is selected from the group consisting of halo, lower alkoxy, dimethylamino and lower alkyl; and $R_3$ is selected from the group consisting of $R_1$, hydrogen and lower alkyl. The preferred phosphine is triphenylphosphine primarily because of its availability and, hence, economy relative to that of other phosphines defined herein.

The terms "lower alkoxy" and "lower alkyl" as used herein are intended to embrace alkoxy and alkyl groups of from 1 to 4 carbon atoms, inclusive.

The 6-demethyl-6-deoxy-6-methylenetetracycline reactants of formula I above are known compounds. Their preparation by 11a-dehalogenation of the corresponding 11a-halo-6-demethyl-6-deoxy-6-methylenetetracyclines by chemical or catalytic reduction is described in detail in J. Am. Chem. Soc. 85, 3943-53 (1963), and in U.S. Pat. Nos. 2,984,646 and 3,183,267. The favored procedure comprises catalytic reduction of the 11a-chloro derivatives in a reaction-inert solvent in the presence of a noble metal catalyst, e.g., palladium, and preferably rhodium, at a temperature of from about 0° to about 60°C. and a hydrogen pressure of from about atmospheric to superatmospheric pressures. Rhodium is especially preferred for this step since it serves as catalyst for hydrogenation of the 6-methylene group. Palladium or platinum afford, at best, very poor hydrogenation of the 6-methylene group under the conditions of this process and are not favored for the dehalogenation step since no advantage is realized by the use of different catalysts when the process is run as a two step, "one-pot" process.

The dehalogenation step, especially when conducted by catalytic reduction over a noble metal catalyst, and particularly over rhodium (supported or unsupported), permits a convenient tie-in with the process of catalytic hydrogenation of the 6-methylene group. The overall process, beginning with an 11a-halo, especially an 11a-chloro-6demethyl-6-deoxy-6-methylenetetracycline, becomes in fact a "one-pot" process. To the reaction mixture containing the 11a-deshalo compound, produced under the conditions described above, triphenylphosphine (or other appropriate phosphine as defined herein) and usually additional catalyst, preferably rhodium-on-carbon, are added and the resulting mixture contacted with hydrogen under conditions described herein. If palladium is used in the dehalogenation step, the addition of rhodium is necessary to achieve satisfactory hydrogenation of the 6-methylene group. If rhodium is used for dehalogenation, it can be added all at once or stepwise as is discussed below:

A preferred embodiment of this invention comprises hydrogenation of an acid addition salt of the 11a-chloro derivative over 5% rhodium-on-carbon in a reaction-inert medium, e.g., methanol, at pressures of from subatmospheric to superatmospheric and at temperatures of from about 0°C. to about 60°C. Sufficient hydrogen is introduced to achieve only 11a-dechlorination. The preferred salts of the 11a-chloro derivative are the p-toluenesulfonate, perchlorate and perborate salts. These salts are preferred since, as noted above, such salts of the 11a-deschloro compounds appear to be of especial value in the subsequent hydrogenation of the 6-methylene group. Other salts of value for the 11a-dechlorination are the hydrochlorides and sulfosalicylates.

This method is especially preferred for large scale reactions since the reaction mixture of the 11a-dechlorinated compound then contains a portion of the preferred catalyst for the final hydrogenation step. Additionally, an amount of acid equivalent on a molar basis to the 11a-chloro compound converted to 11a-deshalo compound is produced thus obviating the need to add more acid. It is then only necessary to add the remaining portion of the rhodium catalyst (rhodium-on-carbon is preferred) and a suitable phosphine, preferably triphenylphospine, to continue the process.

A further advantage of beginning with the appropriate 11a-chloro derivative is the fact that any of the 11a-chloro reactant which is not dehalogenated is carried over to the next step of the process thus affording further opportunity for additional dehalogenation to occur.

When the herein described process is run as a one-pot process beginning with an 11a-chloro derivative of a compound of formula I, dehalogenation is accomplished by catalytic reduction. The amount of catalyst, preferably 5% rhodium-on-carbon, used is a catalytic amount, said expression having the previously given definition. Suitable solvents are lower alkanols, e.g. methanol, ethanol as well as a variety of other solvents such as those enumerated above in connection with the hydrogenation of the 6-methylene group.

The dehalogenation reaction mixture is then charged with additional catalyst, e.g. 5% rhodium-on-carbon. The amount of catalyst added at this point can vary widely, e.g., from 1 to 50 times the amount used in the dehalogenation step. For reasons of economy from about 2 to about 25 times the amount of catalyst used in the dehalogenation step is a practical charge of additional catalyst. Alternatively, all the rhodium to be used in the overall reaction can be added in the dehalogenation step, thus necessitating the addition of only an appropriate phosphine in the hydrogenation step. It is, however, preferred to add rhodium to each of the steps of the overall process; about 25 to about 50% of the total amount being added to the 11a-dehalogenation step and the remaining portion to the hydrogenation step.

The phospine can also be added to the reaction mixture prior to the dehalogenation. However, the yields of 6-deoxytetracyclines generally obtained in this manner are less than that obtained when the phosphine is added after the dehalogenation step, that is, after the reaction of about one mole of hydrogen per mole of 11a-halotetracycline compound present.

The amount of phosphine added, preferably triphenylphosphine, can also vary widely. Molar ratios of phosphine to noble metal catalyst of from about 2 to about 10 are satisfactory in the process of this invention. The favored molar ratio is from about 3-9; and the preferred ratio if from about 3 to about 6 moles of phosphine per mole of total noble metal used.

A further preferred embodiment of this invention comprises 11a-dechlorination of an appropriate 11a-chloro-6-demethyl-6-deoxy-6-methylenetetracycline by treatment thereof with a tertiary phosphine. Secondary phosphines or tertiary phosphites can also be used. Tertiary phosphines, especially tertiary aryl phosphines wherein the aryl group is pheny or substituted pheny as defined herein, are preferred because of the favorable yield afforded by such agents.

The process comprises treating the 11a-chloro-6-demethyl-6-deoxy-6-methylenetetracycline, usually as the hydrochloride or p-toluenesulfonate salt since these are the forms in which the 11a-chloro compounds are generally isolated, in a molar proportion of from about one to about three moles of phosphine per mole of 11a-chloro compound. The reaction is conducted in a hydroxylic containing solvent such as water and lower alkanols (preferably methanol or ethanol) at a temperature of from about 20° to the boiling point of the solvent system for periods of up to three hours. To the reaction mixture containing the deshalo compound, a catalytic amount of a noble metal catalyst and an appropriate phosphine as defined herein are added. Hydrogen is then introduced into the system and the hydrogenation of the 11a-deshalo compound carried out in the manner described above.

The reaction mixtures are conveniently monitored and assayed to determine the approximate extent of the reaction and approximate yields of α- to β-isomers by thin layer chromatography on silica gel plates, buffered at pH 6, using the solvent system tetrahydrofuran-water (95-5). The plates are developed with ammonia and visualized under ultraviolet light (336 mu). More precise determination of the extent and yields of the reactions are achieved by high pressure liquid chromatography. This is accomplished using the Chromatronix 3,100 chromatograph (Chromatronix Inc., Berkely, Calif.). The column used is a 2m. × 2.1 mm. column filled with Dupont SAX, a quaternary ammonium substituted methacrylate polymer coated 1% by weight on "Zipax" (registered trademark of E. I. DuPont Denemours and Co. Inc., Wilmington, Delaware).

The solvent system is 0.001M ethylenediaminetetracetic acid, plus 0.005 M sodium acetate adjusted to 6.0 with acetic acid. A pressure of 1,250 lbs. (equal to 0.5 ml. per minute) is used. The instrument has a 12 mu injection valve.

EXAMPLE I

A Parr bottle is charged with 5% rhodium-on-carbon (2.88 g. of 50% wet material; 0.70 mM of rhodium), triphenylphosphine (0.55 g., 2.1 mM) and N-methyl-2-pyrrolidone (10 ml.). The mixture is shaken for 0.5 hour at 70°C. under 10 p.s.i. of nitrogen at the end of which time a slurry of 6-demethyl-6-deoxy-6-methylene-5-hydroxytetracycline hydrochloride (3.70 g., 7.7 mM) and stannous chloride (0.329 g., 1.5 mM) in N-methyl-2-pyrrolidone (40 ml.) is added into the bottle via a syringe. The bottle is then filled with hydrogen at 50 p.s.i. and shaken overnight at 70°C. for 18 hours. Thin layer chromatography of the reaction mixture showed the reaction went to completion to give 96% α- and 4% β-6-deoxy-5-hydroxytetracycline.

The thin layer chromatography is conducted on silica gel plates. The plates are prepared by spraying them to saturation with a pH 6.0 phosphate-citric acid buffer and then drying. The system 95% tetrahydrofuran-5% water is added and the plates developed in ammonia and visualized under 366 mu ultraviolet light. In this system 6-demethyl-6-deoxy-6-methylene-5-hydroxytetracycline has an Rf = 0.31; α-6-deoxy-5-hydroxytetracycline an Rf = 0.50; and β-6-deoxy-5-hydroxytetracycline an Rf = 0.25.

A known mixture of the above compounds is run for comparison.

EXAMPLE II

A Parr bottle is charged with 5% rhodium-on-carbon (0.572 gms., 50% wet material; 0.14 mM of rhodium), triphenylphosphine (0.113 gms., 0.43 mM) and 1.26 ml. concentrated hydrochloric acid followed by a solution of 6-demethyl-6-deoxy-6-methylene-5-hydroxytetracycline hydrochloride (3.39 gms., 7.0 mM) in methanol (35 ml.) containing 7.0 mM of p-toluenesulfonic acid. The bottle is then filled with hydrogen at 50 p.s.i. and shaken overnight at 75°C. for 20 hours. Thin layer chromatography of the reaction mixture showed predominantly α-6-deoxy-5-hydroxytetracycline and trace levels of starting materials and 6β-epimer.

EXAMPLE III

A stainless steel autoclave is charged with 2.88 gms. of 5% rhodium-on-carbon (50% wet, 0.70 mM of the rhodium) tri-(4-chlorophenyl)phosphine (0.76 gms., 2.1 mM) and a solution of 6-demethyl-6-deoxy-6-methylene-5-hydroxytetracycline (33.9 gms., 70.0 mM) in 360 cc. methanol containing 70.0 mM of p-toluenesulfonic acid. The reaction mixture is pressurized with hydrogen gas to 200 p.s.i., temperature adjusted to 75°C. and the reaction mixture stirred for 17 hours. High pressure chromatography of the reaction mixture indicates the presence of 81% α-6-deoxy-5-hydroxytetracycline and 1.6% β-epimer. Addition of 340 cc. 10% aqueous solution of 5-sulfosalicylic acid permits isolation of α-6-deoxy-5-hydroxytetracycline as the 5-sulfosalicylic acid salt in 80% yield.

EXAMPLE IV

A Parr bottle is charged with 5% rhodium-on-carbon (2.88 gms., 50% wet material; 0.70 mM of rhodium), tri-(4-chlorophenyl)phosphine (0.76 gms., 2.1 mM) in 13 cc. methanol. The mixture is shaken for a half-hour at 62°C., under nitrogen atmosphere, at the end of which time a solution of 3.39 gms., 7.0 mM, of 6-deoxy-6-demethyl-6-methylene-5-hydroxytetracycline hydrochloride in 37 cc. of methanol, containing 7.0 mM of p-toluenesulfonic acid, is added. The bottle is then filled with hydrogen at 50 p.s.i. and shaken overnight at 75°C. for 18 hours. High pressure liquid chromatography of the reaction mixture indicates the presence of 80% α-6-deoxy-5-hydroxytetracycline and 1.5% 6β-epimer. α-6-deoxy-5-hydroxytetracycline may be isolated in 78% yield as the 5-sulfosalicyclic acid salt.

EXAMPLE V

The procedure of Example I is repeated but using the following acid addition salts of 6-demethyl-6-deoxy-6-methylene-5-hydroxytetracycline and the conditions of temperature, pressure, solvent and phosphine listed below:

rhodium-on-carbon (2.88 g. of 50% wet material; 0.70 mM of rhodium) and triphenylphosphine (0.55 g., 2.1mM). The bottle is pressurized to 50 p.s.i. with hydrogen (after appropriate purging) and shaken at 75°C. overnight. The reaction mixture is cooled, methanol (30 ml.) and gaseous hydrogen chloride (2 molar equivalents) added. The slurry is filtered and the filtrate diluted to twice its volume with water. Sulfosalicylic acid (33 ml. of a 10% aqueous solution) is added to the diluted filtrate and the resulting slurry stirred overnight. The sulfosalicylate salt is filtered off and the filter cake dried (3.65 g.). High pressure liquid chromatography (HPLC) according to the above-mentioned procedure showed 55.5% of 6α- and 1.8% of 6β-deoxy-5-hydroxytetracycline and about 2% of 6-demethyl-6-deoxy-6-methylene-5-hydroxytetracycline present. This yield of 6α-isomer corresponds to 65% based upon the starting 11a-chloro derivative.

EXAMPLE VII

A. In an atmosphere of nitrogen, 5% rhodium-on-carbon (2.88 g. of 50% wet material; 0.70 mM rhodium), triphenylphosphine (0.55 g., 2.1 mM) and N-methyl-2-pyrrolidone (13 ml.) are placed in a Parr bottle, heated and shaken at 70°C. for half-hour. A slurry of 6-

EXAMPLE V

| Acid Salt* | Solvent** | T°C. | Time (Hrs.) | P (p.s.i.) | $R_1$ | $R_2$ | $R_3$ |
|---|---|---|---|---|---|---|---|
| HCl | NMP | 70 | 28 | 14 | $C_6H_5$ | $C_6H_5$ | $C_6H_5$ |
| HCl | NMP | 70 | 18 | 50 | $4-ClC_6H_4$ | $4-ClC_6H_4$ | $4-ClC_6H_4$ |
| HCl | NMP | 70 | 18 | 200 | $C_6H_5$ | $C_6H_5$ | $C_2H_5$ |
| HCl | NMP | 80 | 20 | 200 | $C_6H_5$ | $C_6H_5$ | H |
| HCl | NMP | 75 | 18 | 50 | $2-ClC_6H_4$ | $2-ClC_6H_4$ | $2-ClC_6H_4$ |
| HCl | NMP | 70 | 18 | 50 | $3-ClC_6H_4$ | $3-ClC_6H_4$ | $3-ClC_6H_4$ |
| HCl | NMP | 70 | 18 | 50 | $4-Me_2NC_6H_4$ | $4-Me_2NC_6H_4$ | $4-Me_2NC_6H_4$ |
| HCl | NMP | 70 | 18 | 100 | $4-Et_2NC_6H_4$ | $4-Et_2NC_6H_4$ | $4-Et_2NC_6H_4$ |
| HCl | NMP | 70 | 18 | 75 | $C_6H_5$ | $C_6H_5$ | $4-ClC_6H_4$ |
| HCl | $CH_3OH$ | 70 | 18 | 75 | $C_6H_5$ | $C_6H_5$ | $4-BrC_6H_4$ |
| HCl | NMP | 75 | 20 | 65 | $C_6H_5$ | $C_6H_5$ | $4-Me_2NC_6H_4$ |
| HCl | NMP | 70 | 18 | 1000 | 4-tolyl | 4-tolyl | 4-tolyl |
| PTS | NMP | 70 | 20 | 200 | 4-tolyl | 4-tolyl | $CH_3$ |
| PTS | NMP | 80 | 18 | 100 | $C_6H_5$ | 4-tolyl | $CH_3$ |
| PTS | NMP | 80 | 18 | 100 | $C_6H_5$ | $4-BrC_6H_4$ | $4-Me_2NC_6H_4$ |
| PTS | NMP | 80 | 18 | 100 | 4-tolyl | 4-tolyl | $4-MeOC_6H_4$ |
| HCl | $CH_3OH$ | 80 | 18 | 100 | $4-ClC_6H_4$ | $4-ClC_6H_4$ | $4-ClC_6H_4$ |
| citrate | $CH_3OH$ | 75 | 24 | 50 | $C_6H_5$ | $C_6H_5$ | $C_6H_5$ |
| tartrate | NMP | 75 | 24 | 50 | 2-tolyl | 2-tolyl | 2-tolyl |
| PTS | THF | 70 | 24 | 50 | $C_6H_5$ | $C_6H_5$ | $C_6H_5$ |
| PTS | THF | 60 | 36 | 100 | $C_6H_5$ | 4-tolyl | $C_2H_5$ |
| PTS | $C_2H_5OH$ | 50 | 18 | 200 | $C_6H_5$ | $4-MeOC_6H_4$ | $n-C_4H_9$ |
| HBr | NMP | 80 | 16 | 100 | $4-ClC_6H_4$ | $4-ClC_6H_4$ | $4-ClC_6H_4$ |
| HCl | dioxane | 80 | 15 | 500 | $C_6H_5$ | $C_6H_5$ | $C_6H_5$ |
| PTS | NMP | 50 | 20 | 2000 | $C_6H_5$ | $C_6H_5$ | $C_6H_5$ |
| PTS | Acetone | 80 | 18 | 1000 | $C_6H_5$ | $C_6H_5$ | $C_6H_5$ |
| PTS | Glyme | 75 | 24 | 1000 | $C_6H_5$ | $C_6H_5$ | $C_6H_5$ |

*PTS = p-toluenesulfonate; THF = tetrahydrofuran; NMP = N-methyl-2-pyrrolidone;
**Glyme = 2-Methoxyethanol

EXAMPLE VI

To a 500 ml. Parr bottle is added 11a-chloro-6-demethyl-6-deoxy-6-methylene-5-hydroxytetracycline p-toluenesulfonate (5.0 g., 7.1 mM), 5% rhodium-on-carbon (100 mg. of 50% wet material; 0.025 mM of rhodium) and methanol (30 ml.). The flask and contents are purged with nitrogen and then hydrogen at 50 p.s.i. introduced into the flask. The bottle is shaken at room temperature overnight. Assay of the reaction mixture by thin layer chromatography according to the procedure given in Example I showed the 11a-deschloro compound to be the predominant product.

The Parr bottle containing the 11a-deschloro compound is purged with nitrogen and charged with 5% demethyl-6-deoxy-6-methylene-5-hydroxytetracycline hydrochloride (3.7 g., 7.72 mM) in N-methyl-2-pyrrolidone (37 ml.) is then added while maintaining a nitrogen atmosphere. The nitrogen is purged, hydrogen (50 p.s.i.) introduced, and the mixture heated to 70°C. and shaken for 16 hours.

Assay of the reaction mixture as in Example I showed 55% of α- and 5% β-6-deoxy-5-hydroxytetracycline, and 45% of starting material to be present.

B. The reaction mixture is filtered and re-charged with 5% rhodium-on-carbon (2.88 g. of 50% wet material) and triphenylphosphne (0.55 g.). Hydrogenation as above for an additional 16 hours showed, upon assay, 82% yield of α- and 3% yield of β-isomer. 15% of starting material still remained.

EXAMPLE VIII

The procedure of Example VII-A is repeated but with the addition of p-toluenesulfonic acid (1.465 g., 7.72 mM) to the initial charge of catalyst and triphenylphosphine.

After 16 hours reaction time, assay showed 82% α- and 2% of β-6-deoxy-5-hydroxytetracycline and 16% starting material.

Further hydrogenation according to Example VII-B showed, upon assay, complete conversion of starting material and a 95% yield of α- and 2% yield of β-6-deoxy-5-hydroxytetracycline. Unknown products accounted for the remaining 3% of material.

EXAMPLE IX

Repetition of the procedure of Example VII-A but using N-methyl-2-pyrrolidone-water (1-1) in place of N-methyl-2-pyrrolidone as solvent afforded 55% α-6-deoxy-5-hydroxytetracycline and 45% unreacted material when assayed by the procedure of Example I.

EXAMPLE X

Repetition of Example VII-A using N-methyl-2-pyrrolidone-methanol (1-1) as solvent in place of N-methyl-2-pyrrolidone showed 80% α-6-deoxy-5-hydroxytetracycline and 20% unreacted material in the reaction mixture.

EXAMPLE XI

The procedure of Example VII-A is repeated but adding $BF_3 \cdot (C_2H_5)_2O$ (0.68 mM) to the original charge of catalyst and triphenylphosphine. Assay of the reaction mixture shows 85% α-6-deoxy-5-hydroxytetracycline, 10% starting material and 5% decomposition products to be present.

EXAMPLE XII

Repetition of the procedure of Example VIII but using tetrahydrofuran as solvent in place of N-methyl-2-pyrrolidone showed, after 16 hours reaction time, 76% α- and 1% β-6-deoxy-5-hydroxytetracycline; and 23% unreacted starting material.

EXAMPLE XIII

Following the procedure of Example I, 6-demethyl-6-deoxy-6-methylenetetracycline is hydrogenated to predominantly the α-isomer.

EXAMPLE XIV

The procedure of Example III is repeated using 6-demethyl-6-deoxy-6-methylenetetracycline as substrate to produce a product consisting primarily of 6α-deoxytetracycline.

EXAMPLE XV 11a-chloro-6-demethyl-6-deoxy-6-methylenetetracycline is hydrogenated according to the procedure of Example VI to give primarily 6α-deoxytetracycline.

EXAMPLE XVI

The procedure of Example VI is repeated but without the addition of triphenylphosphine to the reaction mixture of 11a-deschloro compound.

Assay of the reaction mixture according to the procedure set forth in Example I showed the ratio of β- to α-isomer to be greater than 5 to 1.

EXAMPLE XVII

A solution of 11a-chloro-6-deoxy-6-demethyl-6-methylene-5-hydroxytetracycline p-toluenesulfonate (10.0g., 0.154 mM) in methanol (52 ml.) is added under a nitrogen atmosphere to a Parr bottle, previously flushed with nitrogen, and containing 5% rhodium-on-carbon (0.20g. of 50% wet material, 0.05 mM). The bottle and contents are purged with nitrogen and then hydrogen at 55 p.s.i. introduced into the Parr bottle. The reaction mixture is shaken at 26°C. for approximately 14 hours. Thin layer chromatography of the reaction mixture showed the 11a-deschloro compound and a trace of α-6-deoxy-5-hydroxytetracycline to be present. The bottle is depressurized and then purged with nitrogen.

To the Parr bottle containing the 11a-deschloro compound is added a mixture of 5% rhodium-on-carbon (0.429 g. of 50% wet material, 0.105 mM), triphenylphosphine (0.226 g., 0.86 mM) and methanol (12 ml.). The bottle is purged with nitrogen and then hydrogen and then pressurized to 50 p.s.i. with hydrogen. It is shaken at 68°–72°C. for about 8 hours. The reaction mixture is cooled, removed from the bottle and acidified with concentrated hydrochloric acid (11.0 ml.). The acidified mixture is then filtered, and the solid washed with methanol to give a total filtrate volume of 100 ml. The addition of sulfosalicylic acid to the filtrate according to the procedure of Example VI precipitates 8.85 g. of sulfosalicylate salt. HPLC showed 59.9% of α- and 1.33% of β-6-deoxy-5-hydroxytetracycline and about 0.8% of 6-deoxy-6-demethyl-6-methylene-5-hydroxytetracycline present.

EXAMPLE XVIII

A mixture of 11a-chloro-6-demethyl-6-deoxy-6-methylene-5-hydroxytetracycline p-toluenesulfonate (2.97 g., 4.51 mM), methanol (30 ml.), water (4 ml.) and triphenylphosphine (1.205 g. 4.60 mM) is shaken in a Parr bottle under an atmosphere of nitrogen at room temperature for three hours.

The Parr bottle containing the 11a-deschloro compound is purged with nitrogen and charged 5% rhodium-on-carbon (1.69 g. of 50% wet material; 0.41 mM of rhodium) and triphenylphosphine (0.32 g., 1.23 mM). The bottle is pressurized to 50 p.s.i. with hydrogen (after appropriate purging) and shaken at 75°C. overnight. The reaction mixture is cooled, methanol (30 ml.) and gaseous hydrogen chloride (2 molar equivalents) added. The slurry is filtered and the filtrate diluted to twice its volume with water. Sulfosalicylic acid (33 ml. of a 10% aqueous solution) is added to the diluted filtrate and the resulting slurry stirred overnight. The sulfosalicylate salt is filtered off and the filter cake dried. The principal product is α-6-deoxy-5-hydroxytetracycline.

1. In the process of introducing hydrogen into a reaction-inert solvent medium containing a catalytic amount of rhodium metal and a tetracycline compound selected from the group consisting of a tetracycline base of the formula and acid addition salts thereof wherein:

R is selected from the group consisting of hydrogen and hydroxy; and X is selected from the group consisting of hydrogen, chloro and fluoro;

and maintaining hydrogen in contact with the reaction mixture at a temperature of from about 0° to about 100° C. and at a pressure of from about atmospheric to 2,000 p.s.i. substantial reduction of the 6 methylene group of said tetracycline compound occurs, the improvement which comprises conducting the reaction in the presence of a. from about 2 to about 10 moles, per mole of rhodium metal used, of a compound of the formula $R_1R_2R_3P$ wherein each of $R_1$ and $R_2$ is selected from the group consisting of phenyl and substituted phenyl wherein the substituent is selected from the group consisting of halo, lower alkoxy, dimethylamino, and lower alkyl; and $R_3$ is selected from the group consisting of $R_1$, hydrogen and lower alkyl; and b. from about 1.1 to about 2.0 moles of acid per mole of tetracycline base, said acid being selected from the group consisting of strong mineral acids and organic acids; or from about 0.1 to about 1.0 mole of stannous chloride per mole of tetracycline acid addition salt.

2. The process of claim 1 wherein $R_3$ is $R_1$.

3. The process of claim 2 wherein the rhodium used is rhodium-on-charcoal, the temperature is from about 70°C. to about 95°C., and the pressure is from about one atmosphere to about 1,000 p.s.i.

4. The process of claim 1 wherein R is hydroxyl.

5. The process of claim 4 wherein X is hydrogen.

6. The process of claim 4 wherein X is chloro.

7. The process of claim 5 wherein the molar ratio of acid to tetracycline compound is from about 1.5 to 1 to about 2 to 1.

8. The process of claim 7 wherein p-toluenesulfonic acid is present.

9. The process of claim 7 wherein hydrochloric acid is present.

10. The process of claim 8 wherein each of $R_1$, $R_2$, and $R_3$ is 4-chlorophenyl.

11. The process of claim 8 wherein each of $R_1$, $R_2$, and $R_3$ is phenyl.

12. The process of claim 1 wherein the reaction-inert solvent is selected from the group consisting of methanol, ethanol, acetone, 2-methoxyethanol, N-methyl-2-pyrrolidone, tetrahydrofuran and dioxane.

13. The process of claim 12 wherein from about 5 to about 80 volume percent water is present in the reaction mixture.

14. The process of claim 12 wherein the solvent is methanol.

15. The process of claim 8 wherein the reaction is conducted in the presence of stannous chloride.

16. The process of claim 15 wherein the tetracycline compound is 6-demethyl-6-deoxy-6-methylene-5-hydroxytetracycline hydrochloride.

17. The process which comprises the step of:

a. introducing hydrogen into a reaction-inert solvent medium containing a catalytic amount of rhodium metal and a tetracycline compound selected from the group consisting of a tetracycline base of the formula and acid addition salts thereof, and at least about one mole of acid per mole of tetracycline base present wherein:

R is selected from the group consisting of hydrogen and hydroxy; and X is selected from the group consisting of chloro and fluoro;

and maintaining hydrogen in contact with the reaction mixture at a temperature of from about 0° to about 60°C. and a pressure of from about atmospheric to 2,000 p.s.i. until replacement of X group is substantially complete;

b. adding a further catalytic amount of a rhodium metal to the reaction mixture and from about 2 to 10 moles per mole of total rhodium metal present of a compound of the formula $R_1R_2R_3P$ wherein: each of $R_1$ and $R_2$ is selected from the group consisting of phenyl and substituted phenyl wherein the substituent is selected from the group consisting of halo, lower alkoxy, dimethylamino, and lower alkyl; and $R_3$ is selected from the group consisting of $R_1$, hydrogen and lower alkyl; introducing and maintaining hydrogen in contact with the reaction mixture at a temperature of from about 70°C. to about 95°C. and at a pressure of from about atmospheric to about 2,000 p.s.i. until reduction of the 6-methylene group is substantially complete.

18. The process of claim 7 wherein $R_3$ is $R_1$.

19. The process of claim 18 wherein the rhodium is rhodium-on-carbon.

20. The process of claim 19 wherein R is hydroxy and X is chloro.

21. The process of claim 20 wherein the tetracycline compound is present as an acid addition salt.

22. The process of claim 20 wherein the acid addition salt is the p-toluenesulfonate.

23. The process of claim 20 wherein the acid addition salt is the hydrochloride.

24. The process of claim 22 wherein each of $R_1$, $R_2$, and $R_3$ is phenyl.

25. The process of claim 22 wherein each of $R_1$, $R_2$, and $R_3$ is 4-chlorophenyl.

* * * * *